United States Patent
Kloke et al.

(10) Patent No.: US 11,963,930 B2
(45) Date of Patent: Apr. 23, 2024

(54) TRANSPORT DEVICE FOR MEDICAL CONTAINERS

(71) Applicants: SCHOTT Pharma Schweiz AG, St. Gallen (CH); SCHOTT POONAWALLA PRIVATE LIMITED, Mumbai (IN)

(72) Inventors: Arne Kloke, St. Gallen (CH); Nicole Sahner, Kümmertshausen (CH); Anil Narayan Narvekar, South Goa (IN); Pratul Prakash Potdar, Nani Daman (IN)

(73) Assignees: SCHOTT Pharma Schweiz AG, St. Gallen (CH); SCHOTT Poonawalla Private Limited, Mumbia (IN)

( * ) Notice: Subject to any disclaimer, the term of this patent is extended or adjusted under 35 U.S.C. 154(b) by 503 days.

(21) Appl. No.: 17/144,494

(22) Filed: Jan. 8, 2021

(65) Prior Publication Data
US 2021/0212897 A1 Jul. 15, 2021

(30) Foreign Application Priority Data

Jan. 10, 2020 (IN) .............................. 202011001199
Apr. 2, 2020 (EP) ..................................... 20167818

(51) Int. Cl.
*B65D 25/10* (2006.01)
*A61J 1/16* (2023.01)
*B65D 1/36* (2006.01)
*C08K 3/34* (2006.01)
*C08L 23/12* (2006.01)

(52) U.S. Cl.
CPC ...... *A61J 1/16* (2013.01); *B65D 1/36* (2013.01); *B65D 25/108* (2013.01); *C08K 3/346* (2013.01); *C08L 23/12* (2013.01); *C08K 2201/005* (2013.01)

(58) Field of Classification Search
CPC .... C08L 9/06; C08L 2205/03; C08F 2810/00; C08F 10/10; A61J 1/16; B65D 25/108
See application file for complete search history.

(56) References Cited

U.S. PATENT DOCUMENTS

| | | | |
|---|---|---|---|
| 4,939,027 A | 7/1990 | Daimon et al. | |
| 2011/0172353 A1 | 7/2011 | Matsunaga et al. | |
| 2014/0027333 A1* | 1/2014 | Pawlowski | ............... B01L 9/06 248/346.03 |

FOREIGN PATENT DOCUMENTS

| | | | |
|---|---|---|---|
| EP | 1 138 390 A1 | 10/2001 | |
| EP | 2330139 A1 * | 6/2011 | ............. C08F 10/06 |
| GB | 2 337 035 A | 11/1999 | |

OTHER PUBLICATIONS

Extended European Search Report dated Mar. 18, 2021 for European Patent Application No. 20197411.0 (7 pages).

* cited by examiner

*Primary Examiner* — Robert D Harlan
(74) *Attorney, Agent, or Firm* — Taylor IP, P.C.

(57) ABSTRACT

A transport device for medical containers includes a carrier plate which has openings for receiving medical containers, and optionally a trough-shaped container which is formed such that the carrier plate can be inserted in the trough-shaped container. The carrier plate contains a polymer and 7.5 to 50 wt.-% inorganic particles. The optional trough-shaped container contains a polymer and optionally 7.5 to 50 wt.-% inorganic particles.

24 Claims, 1 Drawing Sheet

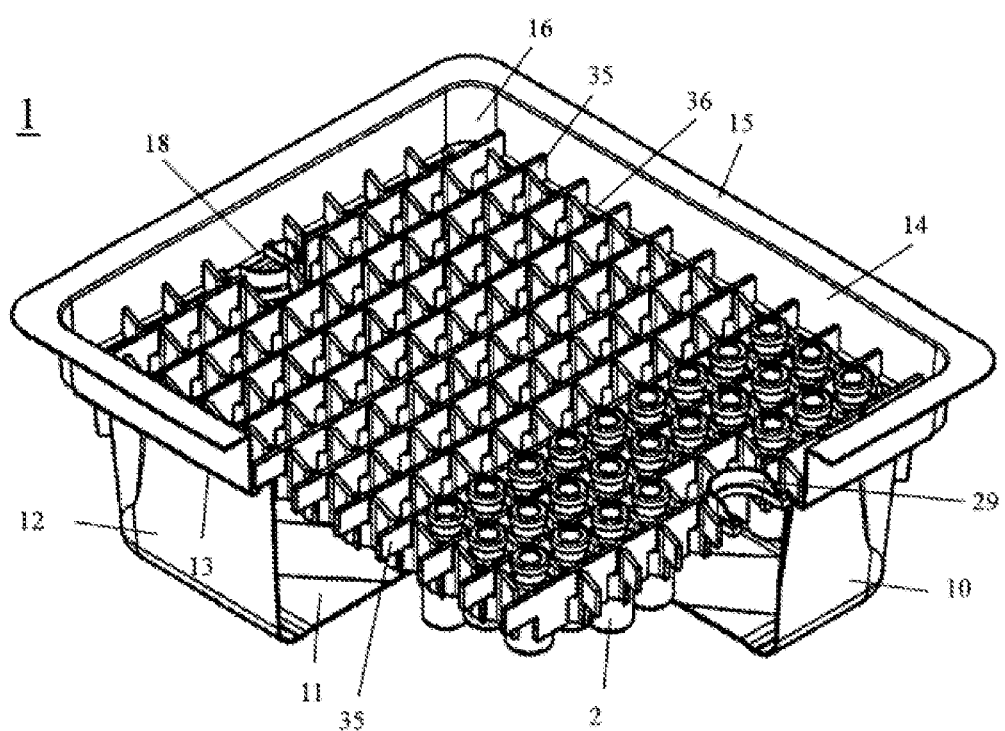

TRANSPORT DEVICE FOR MEDICAL CONTAINERS

CROSS REFERENCE TO RELATED APPLICATIONS

This application claims priority to European Patent Application No. EP 20167818.2 filed on Apr. 2, 2020, which is incorporated in its entirety herein by reference. This application also claims priority to Indian Patent Application No. IN 202011001199 filed Jan. 10, 2020, which is incorporated in its entirety herein by reference.

BACKGROUND OF THE INVENTION

1. Field of the Invention

The invention relates to a transport device for medical containers, including a carrier plate which has openings for receiving the medical containers, and optionally a trough-shaped container which is formed such that the carrier plate can be inserted in the trough-shaped container.

2. Description of the Related Art

Transport devices are known in numerous variants. They generally contain a carrier plate made of a polymer and having a plurality of openings for receiving medical containers. The openings are shaped in such a way that the medical containers can be arranged in them with a firm seat. Various sizes of carrier plates are known. Commonly, the carrier plates have a massive edge surrounding the openings and fine spacers between the openings. The transport devices have the problem that they are not dimensionally stable, especially when they are sterilized. Usually, the transport devices were only used once. However, recently the reduction of polymer products becomes more and more relevant and thus, the demand for polymer products which can be reused has been continuously growing. An example of a transport device is disclosed in EP 1138390 A1.

SUMMARY OF THE INVENTION

In some exemplary embodiments provided according to the present invention, a transport device for medical containers includes a carrier plate having a plurality of openings for receiving medical containers, the carrier plate containing a polymer and 7.5 to 50 wt.-% inorganic particles.

In some exemplary embodiments provided according to the present invention, a transport device for medical containers includes a trough-shaped container containing a polymer and 7.5 to 50 wt.-% inorganic particles and a carrier plate inserted in the trough-shaped container and having a plurality of openings for receiving medical containers. The carrier plate contains a polymer and 7.5 to 50 wt.-% inorganic particles.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawing, wherein:

the sole FIGURE is a partially cut-away perspective view of an exemplary embodiment of a transport device provided according to the present invention.

The exemplification set out herein illustrates one embodiment of the invention and such exemplification is not to be construed as limiting the scope of the invention in any manner.

DETAILED DESCRIPTION OF THE INVENTION

Exemplary embodiments provided according to the present invention are related to a transport device for medical containers, including a carrier plate which has a plurality of openings for receiving the medical containers, and optionally a trough-shaped container which is formed such that the carrier plate can be inserted in the trough-shaped container. The carrier plate contains a polymer and 7.5 to 50 wt.-% inorganic particles. The trough-shaped container, when included, contains a polymer and optionally 7.5 to 50 wt.-% inorganic particles.

Medical containers, in particular packaging materials made of glass or polymer for medically effective substances, such as vials, bottles, ampoules, syringe ampoules, cylinders, syringe bodies, syringes, cartridges and carpoules are known in a wide variety of designs. These medical containers typically have a circular cross-section. However, they may also have a polygonal cross-sectional area. They may be filled or unfilled, such as filled with medically effective substances.

Such medical containers are typically first manufactured in a glass or polymer processing plant and then transported to a medical plant where they are filled. A number of processing steps are necessary both during the manufacture of the medical container and during its filling, such as washing, sterilizing, packaging, transporting, siliconizing, etc. The process is carried out in a controlled manner.

The handling, transport and storage of such medical containers poses particular problems. A major reason for this is that these medical containers are mass-produced articles and therefore cannot be handled individually, but can, for economic reasons, only be handled automatically in ordered batches or magazined in transport devices including a carrier plate, sometimes also called nest or tray.

The transport devices may be sterilized, such as steam-sterilized between 100 and 130° C. They can be sterilized either before use or when the medical containers are already in the openings. The carrier plates may be sterilized alone or when they are inserted in a trough-shaped container, sometimes also called a "tub." Thereby the problem arises that shrinking and bending of portions of the transport devices, e.g. the carrier plate and the trough-shaped container, occur. In addition, after sterilization of the carrier plate alone, the carrier plate does not fit tightly in the trough-shaped container due to shrinking and bending. Furthermore, it was recognized that portions of the transport devices shrink over a certain period, also after the first sterilization, which in turn causes the problem that if the transport devices are not used within a short period after production or sterilization, shrinking has been observed.

As a consequence, the undesired changed geometry of the transporting device causes problems regarding tolerances of the position of the medical containers. Since the allowed tolerances during filling and closing of the medical containers with plugs are very small, problems and consequently failures of the machines occur.

Furthermore, in order to save material and manufacturing costs and to reduce plastic waste, it may be advantageous if the transport devices are used several times. For example, it may be desirable to clean and sterilize the transport devices after use and then reuse the transport device. However, it was observed that during consecutive reuse cycles, the above-described problem cumulatively increases. In particular, the problem regarding tolerances of the position of openings increases.

A further problem is the stability of the transport device, especially the carrier plate, itself. Prior art transport devices bow due to the flexibility of the polymer if they are equipped with the medical containers and especially when the transport devices are equipped with filled medical containers. This can cause the problem that medical containers can clink together. In addition, it was recognized that if the transport devices were sterilized, the problem of bending and warpage of the transport devices further increases.

Exemplary embodiments disclosed herein provide a transport device for medical containers, which overcome the above-described drawbacks. Particularly, exemplary embodiments disclosed herein provide a transport device for medical containers having improved dimensional stability and stiffness, especially over time, and an improved resistance against humidity and temperature stress related to sterilization; and having improved dimensional stability and stiffness when it is reused and subjected to several sterilization processes.

It has been surprisingly observed that a transport device for medical containers, including a carrier plate which has a plurality of openings for receiving the medical containers, and optionally a trough-shaped container which is formed such that the carrier plate can be inserted in the trough-shaped container; the carrier plate containing a polymer and 7.5 to 50 wt.-% inorganic particles, and the trough-shaped container containing a polymer and optionally 7.5 to 50 wt.-% inorganic particles, the above-described drawbacks are overcome and the transport containers exhibit improved dimensional stability and stiffness.

Exemplary embodiments disclosed herein are provided on the consideration that the problems regarding the transport, filling and closing of the medical containers with plugs, especially after sterilization, increase and increase further over the lifespan of the transport device, i.e., they increase overt time and also with the number of reuses. Since the medical containers are filled and closed when they are already placed in the transport device, it was realized that the positioning uncertainties are caused by a continuous deformation of the transport device. In particular, it was realized that the carrier plates and the openings for the medical containers shrink already after the first sterilization and shrink further over time. This results in an exceeding of the positioning tolerance of the openings, which has a drastic disadvantage since the alignment of the plugs for closing the medical containers is usually based on the dimensions of the carrier plate.

It was realized that the high temperatures, e.g., up to 121° C., that occur during steam sterilization are the cause of the deformations. Conventional polymers used for the transport devices deform, bend, and shrink when continuously subjected to steam sterilization. In order to avoid this, several measures could be taken. For example, other sterilization methods could be used, however, therefore new machines have to be purchased and in addition, other sterilization methods complicate the entire reusing process. Thus, instead of improving the sterilization methods, it would be beneficial to improve the polymer itself With extensive experimental efforts, it has been surprisingly observed that by adding inorganic particles to the polymer, shrinking and bending of carrier plate during sterilization is reduced and the stability and dimensional stability of the carrier plate can be improved. Moreover, it has been surprisingly observed that by adding the inorganic particles to the polymer, shrinking and bending can be reduced when the transport device is stored over a long period or reused, especially when the transport device is subjected to several sterilization processes.

In addition, the inorganic particles increase the gliding properties of the polymer which is an advantage for use on filling lines. These improved gliding properties also reduce the risk of abrasion during filling. Furthermore, the uptake of moisture is reduced which further increases the form stability of the transport device and extends the shelf life.

Consequently, the transport of the medical containers in the transport device disclosed herein is safer and the processing steps, e.g. washing, sterilizing, packaging, transporting, siliconizing, can be conducted more accurately. In addition, the transport device exhibits an improved shelf life and can be reused and sterilized several times.

If the concentration of the inorganic particle is 7.5 wt.-% or higher, the amount is sufficient to guarantee the above-mentioned dimensional stability.

If the concentration is 50 wt.-% or less, the amount still enables a suitable mold flow during injection molding. Furthermore, if the amount of inorganic particles is higher than 50 wt.-%, the elasticity of the side walls of the openings decreases drastically and breaking may occur when the medical containers are inserted in the openings of the carrier plate.

Thus, if the concentration of the inorganic particles is 7.5 to 50 wt.-%, such as 10 wt.-% to 40 wt.-%, 15 wt.-% to 30 wt.-%, or about 25 wt.-%, on the one hand sufficient stability is obtained and on the other hand enough elasticity is maintained.

Herein, "inorganic particles" means that the particles are free of carbon. However, they may contain carbon as an impurity. The inorganic particles may have any color. In some embodiments, the inorganic particles are natively white.

Any inorganic particles can be used. Examples of inorganic particles are mineral fillers, e.g., talcum, glass, titanium dioxide, chalk, mica, silica, wollastonite, and ceramic. In some embodiments, the inorganic particles contain oxides of silicon or the inorganic particles are talcum or glass. The inorganic particles may have any shape, e.g., powders, fibers, platelets, grains, etc. Powders may provide for an easy workability.

The inorganic particles may contain moisture. However, the workability improves when the water content of the inorganic particles is 5 wt.-% or lower, such as 3 wt.-% or lower or 1 wt.-% or lower.

The inorganic particles may have any size. However, if the particle size of 90% or more, such as 95% or more or about 100%, of the inorganic particles (with regard to the number of particles) is 0.1 to 1000 µm, such as 1 to 500 µm, 10 to 100 µm, or 10 to 50 µm, the handling and the workability of the polymer material comprising the inorganic particles increases.

Any polymer may be used. The polymer may be a thermoplastic. In some embodiments, the polymer is selected from a group consisting of poly(methyl methacrylate) (PMMA), acrylonitrile butadiene styrene (ABS), polybenzimidazole (PBI), polycarbonate (PC), polyether sulfone (PES), polyether ether ketone (PEEK), polyethylene (PE), polypropylene (PP), polyphenylene sulfide (PPS), polyvinyl chloride (PVC), polytetrafluoroethylene (PTFE), polyamide (PA), polylactic acid (PLA), polyethylenterephthalate (PET), polystyrene (PS), polyoxymethylene (POM) and any combination thereof; more preferably the polymer is polyethylene (PE), polyoxymethylene (POM) and/or polypropylene (PP). Polypropylene is particularly suitable for the abovementioned applications and shows also a particularly high dimensional stability in combination with the inorganic particles. In some embodiments of a transport device, the polymer is polypropylene and the inorganic particles are talcum.

The carrier plate may contain 35 wt.-% or more, such as 40 wt.-% or more, 45 wt.-% or more, 50 wt.-% or more, 60 wt.-% or more, 65 wt.-% or more, 70 wt.-% or more, 75 wt.-% or more, 80 wt.-% or more, 85 wt.-% or more, 90 wt.-% or more, and/or 92.5 wt.-% polymer.

The melting point of the polymer containing the inorganic particles is not particularly limited. However, if the melting point of the polymer containing the inorganic particles is high, sterilization, especially steam sterilization, can be conducted up to higher temperatures. In contrast, if the melting point is too high, workability goes down and required energy to melt the polymer increases. Thus, in some embodiments the melting point of the polymer containing the inorganic particles is 100° C. to 300° C., such as 110° C. to 250° C., 120° C. to 200° C., or 125° C. to 170° C.

The resistance to moisture swelling can be determined by storing the carrier plate and trough-shaped container in water at 50° C. for 4 weeks. If the weight increase is small, the resistance against moisture, which occurs in stream sterilization, is increased. Thus, in some embodiments the weight increase of the carrier plate when stored in water at 50° C. for 4 weeks is 1 wt-% or less, such as 0.5 wt-% or less or 0.2 wt-% or less.

Furthermore, the carrier may contain further admixtures and/or colorants. However, in some embodiments the carrier only consists of the polymer and the inorganic particles.

Regarding the physical appearance, the transport device may contain a carrier plate in which the plurality of openings is arranged in at least one row, such as at least two rows, with the rows being offset to each other.

Such carrier plates are particularly suited for storage, reuse, and refilling. The openings may be shaped in such a way that the medical containers can be arranged in them with a firm seat. The size of the carrier plate is not particularly limited. The larger the carrier plate, the higher the number of openings. The smaller the carrier plate, the less clinking together of the medical containers may occur. Thus, if the carrier plate has a length and a breadth of each 10 to 50 cm, such as 15 cm to 30 cm, the carrier plate exhibits the best stability to number of openings ratio.

The wall thickness of the carrier plate is not particularly limited. However, a huge difference in material thickness may lead to different shrinking ratios within the carrier plate. Thus, if the wall thickness of the carrier plate is 2.5 mm or less, such as 0.4 to 2.0 mm, 0.6 to 1.5 mm, or 0.8 to 1.2 mm, tension within the carrier plate can be reduced and the dimensional stability after sterilization is improved.

Consequently, the best stability to number of openings ratio and dimensional stability after sterilization exhibits a carrier plate wherein a length and a breadth of the carrier plate is each 10 to 50 cm, such as 15 cm to 30 cm, and a wall thickness of the carrier plate is 0.4 to 2.0 mm, such as 0.8 to 1.5 mm or 0.8 to 1.2 mm.

The number of openings for receiving the medical containers is not particularly limited. However, the higher the number of medical containers, the stronger and more resistant must a carrier plate be. Thus, the positive effect of a carrier plate provided according to the present invention can be particularly recognized if the carrier plate contains 10 to 500, such as 30 to 400, 50 to 350, 100 to 300, 150 to 250, or 180 to 230, openings for receiving the medical containers.

The volume of the medical containers is not particularly limited. However, the higher the volume of medical containers, the stronger and more resistant a carrier plate must be. Thus, the positive effect of a carrier plate provided according to the present invention can be particularly recognized if the transport device contains a carrier plate comprising medical containers having a huge volume or weight. In contrast thereto, due to production processes and handling, medical containers having a small volume may be preferred. Thus, in some embodiments, the transport device for medical containers contains a carrier plate which has a plurality of openings for receiving the medical containers, the carrier plate containing medical containers, the medical containers having a volume of 0.1 ml or more and 1000 ml or less, such as 0.2 ml or more and 500 ml or less; 0.5 ml or more and 200 ml or less; 1 ml or more and 100 ml or less; 3 ml or more and 50 ml or less; 4 ml or more and 20 ml or less; or 5 ml or more and 10 ml or less. In some embodiments, the transport device for medical containers contains a carrier plate which has a plurality of openings for receiving the medical containers, the carrier plate containing medical containers, the medical containers are filled and have a weight of 0.1 g to 1100 g, such as 0.2 g to 600 g, 0.6 g to 250 g, 5 g to 100 g, or 5 g to 55 g.

Furthermore, the transport device may contain a trough-shaped container which is formed such that the carrier plate can be inserted in the trough-shaped container. In some embodiments, the trough-shaped container is formed in such a way that the carrier plate is held tightly. Such a transport medical container is particularly suited to carry the carrier plate with the medical containers and can be easily sealed after the medical containers have been filled and closed with plugs. The trough-shaped container, if present, may also contain inorganic particles. If present, these inorganic particles are the same as described above. In addition, the transport device can contain further stabilizing elements or protection layers, e.g., around the trough-shaped container.

Herein, all exemplary embodiments and restrictions of the carrier plate, especially that of the polymer and the inorganic particles, also apply for the trough-shaped container.

The carrier plate and trough-shaped container may have the same or different types and contents of inorganic particles and polymer. However, if the types and contents of inorganic particles and polymer of the carrier plate and the trough-shaped container are the same, the stability and shrinking of both is almost similar, and they fit tightly even after sterilization.

If the carrier plate and the trough-shaped container contain a polymer, such as polypropylene, and 7.5 to 50 wt.-% inorganic particles, such as talcum, a particularly high dimensional stability during steam sterilization of both is achieved and thus, the material is particularly suited for a high number of reuse cycles.

In some embodiments, the carrier plate, and/or the carrier plate and the through-shaped container, and/or the carrier plate and the through-shape container and the medical containers, is/are fully enclosed by at least one sterile bag.

An exemplary embodiment provided according to the present invention will now be described with reference to the accompanying drawing. The sole FIGURE shows a transport device with a carrier plate for medical containers and a trough-shaped container, the trough-shaped container being partially cut-out.

The transport device 1 according to the sole FIGURE may be used, as described further herein, for concurrently supporting a plurality of medical containers 2 for storage of substances for cosmetic, medical or medical applications in an array configuration, in particular in a matrix configuration with regular intervals between the medical containers 2 along two different directions in space, such as along two mutually orthogonal spatial directions. Examples of such medical containers 2 are, e.g., vials, which have a cylindrical basic shape having a cylindrical side wall with—within tolerances—constant inner and outer diameters, which project vertically from a flat vial bottom, which merges in a constricted neck portion of a relatively short axial length near the upper open end of the vial and then merges in a widened upper rim, which has a larger outer diameter than the associated neck portion and is configured for connection to a closure member such as a plug.

Such vials are radially symmetric and are made of a transparent or colored glass or of a suitable polymer by blow molding or polymer injection molding techniques, and in general can be internally coated so that the material of the vial emits minimal impurities to the agent to be received. Other examples of a medical container are ampoules, syringe ampoules, cylinders, syringe bodies, syringes, cartridges and carpoules. In the general sense of the present invention, such medical containers 2 are used for storage of substances or agents for cosmetic, medical or medical applications, which are to be stored in one or several components in solid or liquid form in the medical containers 2. Especially in the case of glass medical containers, storage periods can amount to many years, notably depending on the hydrolytic resistance of the glass type used. It should be noted that the medical containers 2, in the sense of the present invention, may also have a different profile, for example a square, rectangular or polygonal profile.

For concurrently supporting a plurality of the above mentioned medical containers, a carrier plate 36 is provided as a supporting structure. The carrier plate 36, which is formed of a material as described herein, e.g., by injection-molding. The carrier plate 36 contains a plurality of openings 35 that extend in the longitudinal direction of the medical containers 2 to be accommodated and which are coupled with each other. A plurality of medical containers 2 may be supported by friction or may be clamped, such they sit tight in the openings 35. The side walls of the openings 35 may be sufficiently flexible and expandable so that the medical containers 2 can be inserted from above or from below into the openings 35. Due to the elasticity of the side walls of the openings 35 also manufacturing tolerances in the axial and/or radial direction of the medical containers may be compensated, in particular in the case of medication medical containers of glass. In particular, medical containers 2 having different diameters may also be supported by one and the same carrier plate 36 by friction.

For the transport and packaging of a carrier plate 36 in the sense of the present invention with the medical containers 2 accommodated therein, a trough-shaped container 10 can be used. According to the sole FIGURE, the trough-shaped container 10 is substantially box-shaped or tub-shaped and has a base 11, a circumferential side wall 12 protruding in vertical direction therefrom, a step 13 protruding substantially rectangular therefrom, a circumferential upper side wall 14 and an upper rim 15 which is formed as a flange. The corners 16 of the trough-shaped container 10 are suitably formed rounded. The upper side wall 14 may be formed inclined at a small angle of inclination with respect to the vertical to the base 11 in order to ease the insertion of the carrier plate 36. Such a trough-shaped container 10 may be formed by injection molding. In particular, both trough-shaped container 10 and carrier plate 36 may be made of the same material.

For receiving the carrier plate 36 in the trough-shaped container 10, the carrier plate 36 may be surrounded by a holding frame which has a supporting web which is formed closed. The carrier plate 36 shown in the sole FIGURE generally may also be clamped in a supporting frame or be clamped along the edge or may be integrally formed with such a supporting frame. For a reliable positioning of the carrier plate 36 in the trough-shaped container 10, the carrier plate 36 and the medical containers 2 may have positioning structures that cooperate with each other, in particular in a positive-fit manner. Thus, positioning structures in the form of projections or recesses or depressions may be formed at an appropriate position, in particular on the step 13 or on the supporting surfaces 18 of the trough-shaped container 10, which co-operate in a positive-fit manner with corresponding recesses or depressions or projections of the supporting structure for precisely positioning the carrier plate 36 in the trough-shaped container 10. To this end, a plurality of pin-like protrusions may be formed on the step 13 which engage in corresponding centering openings formed in the supporting structure. According to the sole FIGURE, the step 13 of the trough-shaped container 10 is formed as a circumferential, flat supporting surface on which the carrier plate 36 is directly supported. According to some embodiments, also additional supporting surfaces or supporting elements, in particular in the form of protrusions, may be formed on the side walls 12 of the trough-shaped container 10, as described further herein. In this manner, the carrier plate 36 can be positioned precisely in the trough-shaped container 10 and thus the plurality of medical containers 2 can be positioned and held in a regular array and at precisely defined positions in a trough-shaped container 10 with standardized dimensions. In particular, it can be ensured in this way that all bottoms of the medical containers are positioned in a plane defined jointly and parallel to the base 11 or to the upper rim 15 of the trough-shaped container 10.

Although the bottom 11 of the trough-shaped container 10 in the sole FIGURE is shown as a closed bottom which is formed integrally with the side wall 12, the lower end of the trough-shaped container 10 may also be formed open in the manner of the upper end, in particular with a flange-like bottom rim in the manner of the upper rim 15 so that the bottoms of the medical containers are freely accessible from the underside of the trough-shaped container 10.

As shown in the sole FIGURE, in the array configuration, the plurality of medical containers 2 are supported distributed along two mutually orthogonal directions in a plane and at predetermined constant intervals. In principle, also other regular arrangements are conceivable, e.g., rows or columns of medical containers 2 may also be disposed offset to each other by a predetermined length, namely in a periodic configuration having a predetermined periodicity. Thus, automated processing systems may expect the medical containers 2 at precisely predetermined positions upon their transfer to a processing station, which significantly reduces the efforts required for automation. As explained in more detail further herein, according to the present invention the medical containers 2 may also be processed further jointly while being within the carrier plate 36 or the trough-shaped container 10.

For enabling an easy insertion of the carrier plate 36 into the trough-shaped container 10 and removal from the latter, access apertures 29 may be formed on two longitudinal sides of the carrier plate 36, via which gripping arms or the like may grab the carrier plate 36. As can be seen in the sole FIGURE, the access apertures 29 are offset from one another by a row which further facilitates an unambiguous positioning of the carrier plate 36 in the trough-shaped container 10.

As already indicated previously, the medical containers 2 are delivered in sterile form after their manufacturing, and the empty medical containers 2 are brought into the filling machine with the aforementioned transport device 1. For filling, i.e., for inserting the filling tubes into the medical containers 2 and for the subsequent insertion of the settling tubes into the medical containers 2 filled with liquid, these must be aligned geometrically exactly in a separate step, since the holder does not guarantee this alignment from the start. This alignment is particularly important when placing the abovementioned plugs in the medical container bodies, as the set tubes may have a diameter that is only slightly smaller than the inner diameter of the syringe bodies.

EXAMPLES

Experiments have been conducted to compare the dimensional stability. In the experiment, a carrier plate consisting of polypropylene and a carrier plate, where the carrier plate consists of 70% polypropylene and 30 wt.-% talcum for 3 ml carpules respectively, have been produced. The carrier plates have both the same shape and a length of 23 cm, a width of 20 cm and a wall thickness of 1.38 to 1.42 mm. After 72 h, both were submitted to steam sterilization at 121° C. for 30 minutes.

The carrier plate consisting of pure polypropylene showed a shrinkage of 1.51 mm in length and 1.21 mm in width. The carrier plate provided according to the present invention, where the carrier plate consists of 70% polypropylene and 30 wt.-% talcum, only showed a shrinkage of 0.78 mm in length and 0.64 mm in width. Thus, the shrinkage, measured at the outer dimensions of the carrier plate 36, were reduced by circa 50% by way of the admixture of 30 wt.-% talcum. In addition, the carrier plate with talcum was showing less tendency to warpage during sterilization and was substantially stiffer than the one without talcum. Hence, precision of positions and equal height level of the carpules facilitated the automated capturing required for position-tolerance sensitive stoppering.

Further observations of the previously described carriers were carried out for the following two years. Thereby, the carrier consisting of polypropylene showed a further shrinking of 1.3 mm after 2 years, whereas the carrier provided according to the present invention does not show any further shrinking within this time period.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE CHARACTER LIST 1 transport device
2 medical container
10 trough-shaped container
11 base
12 side wall
13 step
14 upper side wall
15 upper rim
16 corner
35 opening
36 carrier plate

What is claimed is:
1. A transport device for medical containers, comprising:
a carrier plate having a plurality of openings for receiving medical containers, the carrier plate containing a polymer and 7.5 to 50 wt.-% inorganic particles, wherein a length and a breadth of the carrier plate are each 10 to 50 cm.
2. The transport device of claim 1, further comprising a trough-shaped container which is formed such that the carrier plate is insertable in the trough-shaped container.
3. The transport device of claim 2, wherein the trough-shaped container contains a polymer and 7.5 to 50 wt.-% inorganic particles.
4. The transport device of claim 3, wherein the trough-shaped container contains 10 wt.-% to 40 wt.-% inorganic particles.
5. The transport device of claim 2, wherein the trough-shaped container contains 35 wt.-% polymer.
6. The transport device of claim 2, wherein the types and contents of inorganic particles and polymer of the carrier plate and the trough-shaped container are the same.
7. The transport device of claim 1, wherein the carrier plate contains 10 wt.-% to 40 wt.-% inorganic particles.
8. The transport device of claim 1, wherein the inorganic particles at least one of contain oxides of silicon or are talcum, glass powder or glass fiber.
9. The transport device of claim 8, wherein the inorganic particles comprise talcum and the polymer comprises polypropylene.
10. The transport device of claim 8, wherein at least one of:
a water content of the inorganic particles is 5 wt.-% or lower; or
a particle size of 90% or more of the inorganic particles is 10 to 100 µm.
11. The transport device of claim 1, wherein the carrier plate contains 35 wt.-% or more polymer.
12. The transport device of claim 1, wherein the polymer is at least one of polyethylene (PE), polyoxymethylene (POM) or polypropylene (PP).
13. The transport device of claim 1, wherein the carrier plate consists of the polymer and the inorganic particles.
14. The transport device of claim 1, wherein a wall thickness of the carrier plate is 2.5 mm or less.
15. The transport device of claim 1, wherein at least one of:
the carrier plate contains 10 to 500 openings for receiving medical containers; or
the carrier plate contains a plurality of medical containers, wherein the medical containers each have a volume of 0.1 ml or more and 1000 ml or less.
16. A transport device for medical containers, comprising:
a trough-shaped container containing a polymer and 7.5 to 50 wt.-% inorganic particles; and
a carrier plate inserted in the trough-shaped container and having a plurality of openings for receiving medical containers, the carrier plate containing a polymer and

7.5 to 50 wt.-% inorganic particles, wherein a length and a breadth of the carrier plate are each 10 to 50 cm.

17. The transport device of claim 16, wherein the polymer of the trough-shaped container and the polymer of the carrier plate are the same and the inorganic particles of the trough-shaped container and the inorganic particles of the carrier plate are the same.

18. The transport device of claim 17, wherein the polymer of the trough-shaped container and the carrier plate is at least one of polyethylene (PE), polyoxymethylene (POM) or polypropylene (PP) and the inorganic particles of the trough-shaped container and the carrier plate at least one of contain oxides of silicon or are talcum, glass powder or glass fiber.

19. The transport device of claim 17, wherein contents of the polymer and the inorganic particles in the trough-shaped carrier and the carrier plate are the same.

20. A transport device for medical containers, comprising:
a carrier plate having a plurality of openings for receiving medical containers, the carrier plate containing a polymer and 7.5 to 50 wt.-% inorganic particles, wherein a wall thickness of the carrier plate is 2.5 mm or less.

21. The transport device of claim 20, wherein the inorganic particles at least one of contain oxides of silicon or are talcum, glass powder or glass fiber.

22. The transport device of claim 21, wherein the inorganic particles comprise talcum and the polymer comprises polypropylene.

23. The transport device of claim 21, wherein at least one of:
a water content of the inorganic particles is 5 wt.-% or lower; or
a particle size of 90% or more of the inorganic particles is 10 to 100 um.

24. The transport device of claim 21, wherein the carrier plate consists of the polymer and the inorganic particles and the carrier plate contains 70 to 92.5 wt.-% polymer and 7.5 to 30 wt.-% inorganic particles.

* * * * *